US012758102B2

(12) United States Patent
Kim

(10) Patent No.: US 12,758,102 B2
(45) Date of Patent: Oct. 13, 2026

(54) 3D-IMAGE ORAL SCANNER WITH STEREO OPTICAL SYSTEM CONFIGURED USING SINGLE CAMERA

(71) Applicant: TEAMNUBIZ CO., LTD., Hwaseong-si (KR)

(72) Inventor: Eun Goo Kim, Eumseong-gun (KR)

(73) Assignee: TEAMNUBIZ CO., LTD., Hwaseong-si (KR)

( * ) Notice: Subject to any disclaimer, the term of this patent is extended or adjusted under 35 U.S.C. 154(b) by 0 days.

(21) Appl. No.: 19/101,367

(22) PCT Filed: Feb. 9, 2023

(86) PCT No.: PCT/KR2023/001873
§ 371 (c)(1),
(2) Date: Feb. 5, 2025

(87) PCT Pub. No.: WO2024/043419
PCT Pub. Date: Feb. 29, 2024

(65) Prior Publication Data

US 2026/0108155 A1 Apr. 23, 2026

(30) Foreign Application Priority Data

Aug. 23, 2022 (KR) ........................ 10-2022-0105801

(51) Int. Cl.
*G02B 30/60* (2020.01)
*A61B 5/00* (2006.01)
*G02B 26/08* (2006.01)

(52) U.S. Cl.
CPC .......... *A61B 5/0088* (2013.01); *A61B 5/0062* (2013.01); *A61B 5/4547* (2013.01);
(Continued)

(58) Field of Classification Search
CPC ... A61B 5/0088; A61B 5/0062; A61B 5/4547; G02B 30/60; G02B 26/0816; G02B 26/0883
See application file for complete search history.

(56) References Cited

U.S. PATENT DOCUMENTS

2007/0038122 A1 2/2007 Geng
2008/0101657 A1 5/2008 Durkin
(Continued)

FOREIGN PATENT DOCUMENTS

JP 2013-537826 A 10/2013
KR 10-2014-0098119 A 8/2014
(Continued)

*Primary Examiner* — Hung Q Dang
*Assistant Examiner* — Jose M Mesa
(74) *Attorney, Agent, or Firm* — Bridgeway IP Law Group, PLLC; Sang Ho Lee; Hyun Woo Shin

(57) ABSTRACT

A 3D-image oral scanner with a stereo optical system configured using a single camera according to the present disclosure includes a stereo image optical unit 3-dimensionally photographing measurement objects in an oral cavity through one camera, wherein the stereo image optical unit includes: a first light path changer changing paths of a first light image and a second light image traveling inside at different angles after reflecting from a measurement object in an oral cavity to an image light path; and one camera sensor taking the first light image and the second light image together that have traveled inside at different angles and of which the paths have been changed by the light path changer.

7 Claims, 5 Drawing Sheets

FRONT CROSS-SECTIONAL VIEW

(52) U.S. Cl.
CPC ..... *G02B 26/0816* (2013.01); *G02B 26/0883* (2013.01); *G02B 30/60* (2020.01)

(56) References Cited

U.S. PATENT DOCUMENTS

| | | | | |
|---|---|---|---|---|
| 2024/0207021 | A1* | 6/2024 | Park | G16H 40/40 |
| 2025/0194913 | A1* | 6/2025 | Kim | A61B 1/00009 |

FOREIGN PATENT DOCUMENTS

| | | | |
|---|---|---|---|
| KR | 10-1610171 | B1 | 4/2016 |
| KR | 10-1874547 | B1 | 7/2018 |

* cited by examiner

FRONT CROSS-SECTIONAL VIEW

3D-IMAGE ORAL SCANNER WITH STEREO OPTICAL SYSTEM CONFIGURED USING SINGLE CAMERA

BACKGROUND

Technical Field

The present disclosure relates to a 3D-image oral scanner. In more detail, the present disclosure relates to a 3D-image oral scanner with a stereo optical system configured using a single camera, the 3D-image oral scanner being able to provides effects of ensuring a spatial degree of freedom and addressing high material costs by reducing the number of camera lens groups from more than 2 to one and by reducing the number of camera sensors from two to one, unlike 3D oral scanners of the related art, of not requiring an additional board for combining images by synchronizing two images, and of reducing the material costs and shortening the development schedule.

Description of the Related Art

In general, an oral scanner is an optical device used to generate a 3D scanning model of dental arch by scanning teeth in a non-contact manner after being inserted into the oral cavity of a dental patient. Such 3D oral scanners are used to scan teeth by being inserted into the oral cavity of patients. By using these devices, the patient's tooth shape information is easily and quickly converted into digital data and acquired, and thus they are widely used in dental treatments such as orthodontics, implants, and prosthetics.

In 3D oral scanners of the related art, that is, oral scanners that implement 3D images in an existing stereo vision manner, at least two or more cameras and an engine or projector capable of projecting lighting patterns are necessarily required.

That is, a lighting pattern generated by an engine is projected to an object through an image-forming lens group and then travels into two cameras arranged in different directions, that is, at different angles and receiving reflection from the object.

Light travels into two image sensors through a camera lens group positioned at the left side and a camera lens group positioned at the right side, whereby images are measured. In this case, a board that combines the images obtained at a high speed through two different cameras into one synchronized image is additionally required.

As described above, due to the two camera lens groups, two image sensors, and board combining two images through synchronization, the overall size of the 3D oral scanners increase and there is a limitation in reduction of weight. Further, there was a problem of high material costs and development expenses.

The present disclosure is proposed to address theses issues, that is, reducing the overall size of a 3D oral scanner, reducing the weight thereof, lowering material costs, and reducing development costs as well.

As a related prior patent document, Korean Patent No. 10-1874547 (title of invention: 3D oral scanner) can be cited. The paten document discloses a 3D oral scanner including: a case that can be inserted into and removed from an oral cavity and having an opening at an end through which an image of the inside of an oral cavity is introduced in the form of light; a pair or lenses disposed in the case and spaced apart from each other in the width direction of the case to transmit incident light from an end of the case through different paths; a pair of imaging boards including an imaging sensor, which receives the light passing through the pair of lenses and generates image information from the light, and disposed in close contact with a side and another side of the case in the width direction; and a pair of light path changers disposed to change the paths of the light passing through the pair of lenses toward the imaging board.

As described above, it can be seen that the 3D oral scanner disclosed in Korean Patent No. 10-1874547 includes two lens groups, two camera image sensors, and a board combining two synchronized images. Accordingly, there is a problem that the overall size of the 3D oral scanner increases, it is limited to reduce the weight, and the material costs and development costs are significantly high.

PRIOR ART DOCUMENT

Patent Document (Patent Document 1) Korean Patent No. 10-1874547 (registered on Jun. 28, 2018), Title of Invention: 3D oral scanner

DETAILED DESCRIPTION

Technical Problem

The present disclosure has been made in an effort to solve the problems described above and an objective of the present disclosure is to provide a 3D-image oral scanner with a stereo optical system configured using a single camera, the 3D-image oral scanner enabling reduction of the overall size, the weight, the material costs, and the development costs as well.

That is, an objective of the present disclosure is to provide a 3D-image oral scanner with a stereo optical system configured using a single camera, the 3D-image oral scanner being able to implement a 3D image by configuring a stereo optical system using one camera lens group and one camera sensor.

An objective of the present disclosure is, through this configuration, provides a 3D-image oral scanner with a stereo optical system configured using a single camera, the 3D-image oral scanner being able to ensure a spatial degree of freedom and address high material costs by reducing the number of camera lens groups from more than 2 to one and by reducing the number of camera sensors from two to one, the 3D-image oral scanner not requiring an additional board for combining images by synchronizing two images, and the 3D-image oral scanner being able to provide an effect of reducing the material costs and shortening the development schedule.

Technical Solution

A 3D-image oral scanner with a stereo optical system configured using a single camera according to an embodiment of the present disclosure for achieving the objectives described above includes a stereo image optical unit 3-dimensionally photographing measurement objects in an oral cavity through one camera, wherein stereo image optical unit includes: a first light path changer changing paths of a first light image and a second light image traveling inside at different angles after reflecting from a measurement object in an oral cavity to an image light path; and one camera sensor taking the first light image and the second light image together that have traveled inside at different angles and of which the paths have been changed by the light path changer.

In this configuration, the first light path changer includes: a first reflective mirror and a second reflective mirror spaced apart from each other to reflect beams of light traveling inside at different angles after reflecting from a measurement object in an oral cavity to a double-sided prism positioned on an image light path; and a double-sided prism reflecting a first light image and a second light image reflecting from the first reflective mirror and the second reflective mirror, respectively, while changing paths of the first and second light images to the image light path on a first surface and a second surface thereof, and the one camera sensor takes the first light image and the second light image together which have traveled inside at different angles and of which the paths have been changed on the first surface and the second surface of the double-sided prism.

In this configuration, it is preferable that the first reflective mirror, the second reflective mirror, and the double-sided prism are integrally manufactured and assembled. Accordingly, it is possible to improve the assembly efficiency of the 3D-image oral scanner with a stereo optical system configured using a single camera.

Further, the 3D-image oral scanner includes an engine having a center axis different from the image light path and making and projecting a structured light pattern, wherein the engine includes: a light unit using a 3-wavelength light source a blue LED; and a second image-forming lens group forming an image using light coming out from the lighting unit.

Further, the 3D-image oral scanner with a stereo optical system configured using a single camera includes a second light path changer changing a path of light coming out through the second image-forming lens group to a path the same as the image light path.

In this configuration, the second light path changer may include a third reflective mirror and a fourth reflective mirror.

Further, the 3D-image oral scanner with a stereo optical system configured using a single camera includes a third reflective mirror and a fourth reflective mirror changing a path of light coming out through the second image-forming lens group to a path the same as the image light path.

In this configuration, the third reflective mirror and the fourth reflective mirror are manufactured and assembly into an integral reflective mirror. Accordingly, it is possible to improve the assembly efficiency of the 3D-image oral scanner with a stereo optical system configured using a single camera.

Further, the 3D-image oral scanner with a stereo optical system configured using a single camera includes a first image-forming lens group between the light path changer and the camera sensor, and the first light image and the second light image that have traveled inside and of which the paths have been changed by the light path changer are taken and sent to the camera sensor through the first image-forming lens group.

Advantageous Effect

According to 3D-image oral scanner with a stereo optical system configured using a single camera of an embodiment of the present disclosure, first, it is possible to reduce the overall size, the weight, and the material costs of an oral scanner and reduce the development costs as well.

Second, unlike the related art, there is provided effects of ensuring a spatial degree of freedom and addressing high material costs by reducing the number of camera lens groups from more than 2 to one and by reducing the number of camera sensors from two to one, of not requiring an additional board for combining images by synchronizing two images, and of reducing the material costs and shortening the development schedule.

Third, the first reflective mirror, the second reflective mirror, and the double-sided prism are integrally manufactured and assembled, whereby it is possible to improve the assembly efficiency of the 3D-image oral scanner with a stereo optical system configured using a single camera. Further, it is possible to fundamentally prevent errors that may be generated when assembling the first reflective mirror, the second reflective mirror, and the double-sided prism that are separately manufactured.

Fourth, the third reflective mirror and the fourth reflective mirror are manufactured into an integral reflective mirror, whereby it is possible to improve the assembly efficiency of the 3D-image oral scanner with a stereo optical system configured using a single camera. Further, it is possible to fundamentally prevent errors that may be generated when assembling the third reflective mirror and the fourth reflective mirror that are separately manufactured.

Meanwhile, the effects of the present disclosure are not limited to the effects described above and other effects can be clearly understood by those skilled in the art from the following description.

BRIEF DESCRIPTION OF THE DRAWINGS

The accompanying drawings of this specification exemplify preferred embodiments and help easy understanding of the present disclosure together with the following detailed description, so the present disclosure should not be construed as being limited to the drawings.

BEST MODE

Hereinafter, preferred embodiments of the present disclosure will be described with reference to accompanying drawings. The terms and words used in the present specification and claims should not be interpreted as being limited to typical meanings or dictionary definitions, but should be interpreted as having meanings and concepts relevant to the technical scope of the present disclosure based on the rule according to which an inventor can appropriately define the concept of the term to describe most appropriately the best method he or she knows for carrying out the invention.

Therefore, the configurations described in the embodiments and drawings of the present disclosure are merely most preferable embodiments but do not represent all of the technical spirit of the present invention. Thus, it should be understood that the present disclosure should be construed as including all the changes, equivalents, and substitutions included in the spirit and scope of the present disclosure at the time of filing this application.

Figure 1:
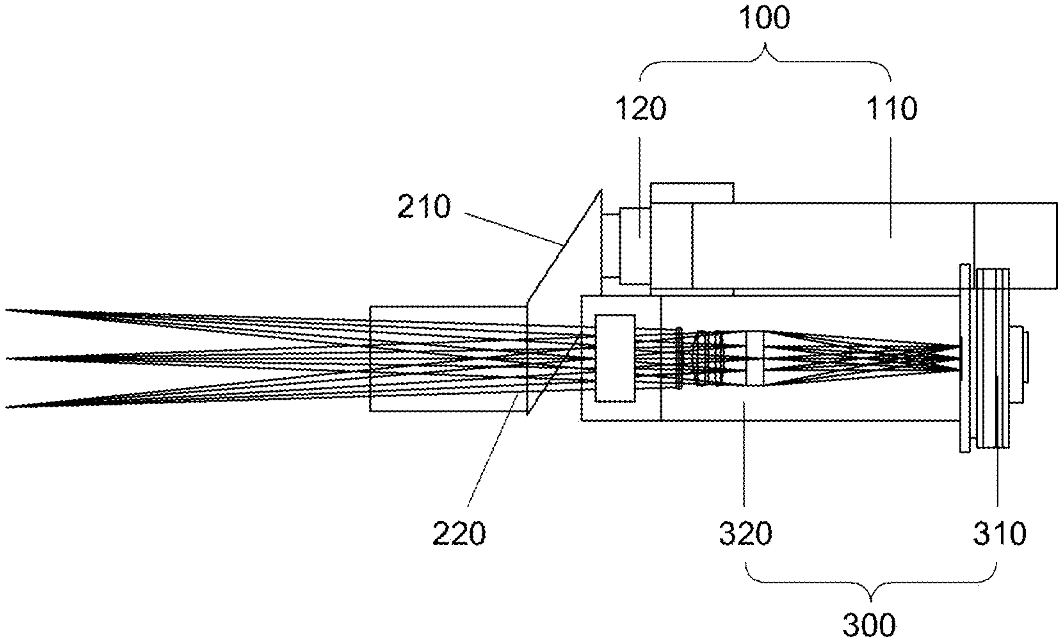
FIG. 1 is a front cross-sectional view of a 3D-image oral scanner with a stereo optical system configured using a single camera according to a preferred embodiment of the present disclosure.
Figure 2:
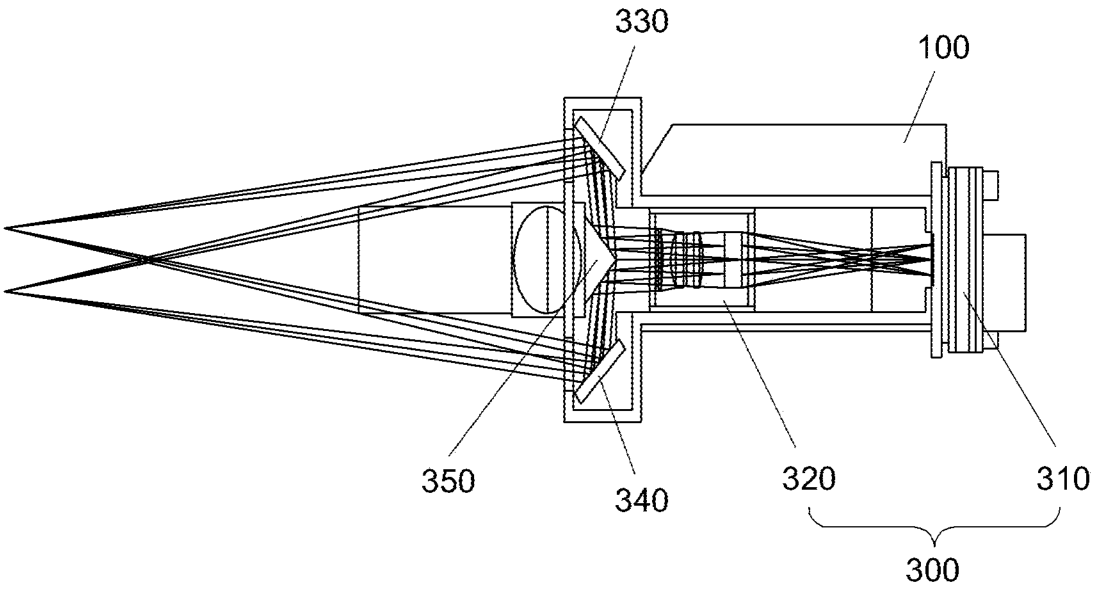
FIG. 2 is a cross-sectional plan view of the 3D-image oral scanner with a stereo optical system configured using a single camera according to a preferred embodiment of the present disclosure.
Figure 3:
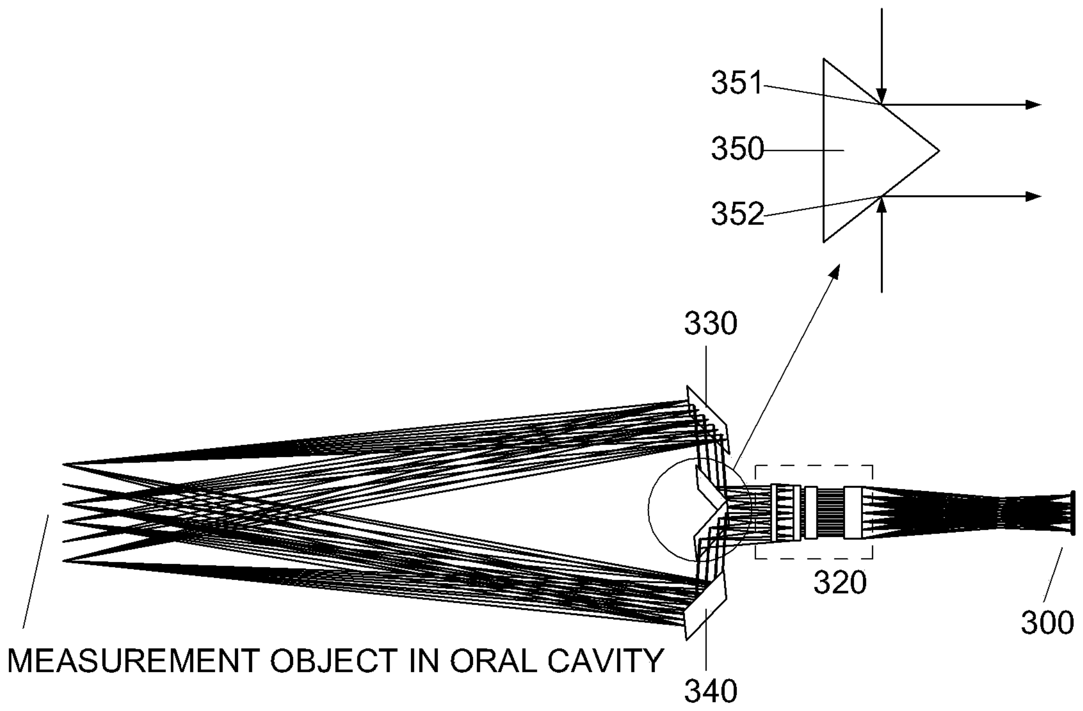
FIG. 3 is a view showing in detail a stereo image optical unit 300 of the 3D-image oral scanner with a stereo optical system configured using a single camera according to a preferred embodiment of the present disclosure.

FIG. 1 is a front cross-sectional view of a 3D-image oral scanner with a stereo optical system configured using a single camera according to a preferred embodiment of the present disclosure, FIG. 2 is a cross-sectional plan view of the 3D-image oral scanner with a stereo optical system configured using a single camera according to a preferred embodiment of the present disclosure, and FIG. 3 is a view showing in detail a stereo image optical unit 300 of the 3D-image oral scanner with a stereo optical system configured using a single camera according to a preferred embodiment of the present disclosure.

The present disclosure is described hereafter with reference to FIG. 1 to FIG. 3. As shown in FIG. 1 to FIG. 3, a 3D-image oral scanner with a stereo optical system configured using a single camera according to the present disclosure includes an engine 100 and a stereo image optical unit 300.

The 3D-image oral scanner that is the objective device of the present disclosure is used to scan teeth by being inserted into the oral cavity of a patient, and, by using the oral scanner, the patient's tooth shape information is easily and quickly converted into digital data and acquired, and thus it can be widely used in dental treatments such as orthodontics, implants, and prosthetics.

In this configuration, the stereo image optical unit 300 is a component that 3-dimensionally photographs measurement objects or target objects in an oral cavity using only one camera unlike the oral scanners of the related art. In general, measurement objects or target objects in an oral cavity refer to objects or things positioned in an oral cavity such as teeth and gums.

The engine 100 is a component that has a center axis, an axis, or a reference different from an image light path of the stereo image optical unit 300 and generates and projects a structured light pattern. The center axis of the engine 100 and the image light path of the stereo image optical unit 300 are parallel with each other and are preferably spaced a predetermined distance apart from each other, but it is not preferable that they are spaced too far apart for a compact 3D-image oral scanner.

The engine 100 includes a lighting unit 110 and a second image-forming lens group 120. The lighting unit 110 may use only a 3-wavelength light source (LED) or, if necessary, a blue LED and is composed of an optical unit and a Digital Micromirror Device (DMD), and a structured light pattern generated by the DMD is projected to measurement objects (teeth, gums) in an oral cavity through the second image-forming lens group 120. It is preferable that the second image-forming lens group 120 is composed of two to six lenses. In detail, the second image-forming lens group 120 can be implemented by five lenses.

As shown in FIG. 1, second light path changers such as a third reflective mirror 210 and a fourth reflective mirror 220 are included to change the light coming out through the second image-forming lens group 120 to a path such as an image light path.

Figure 4:
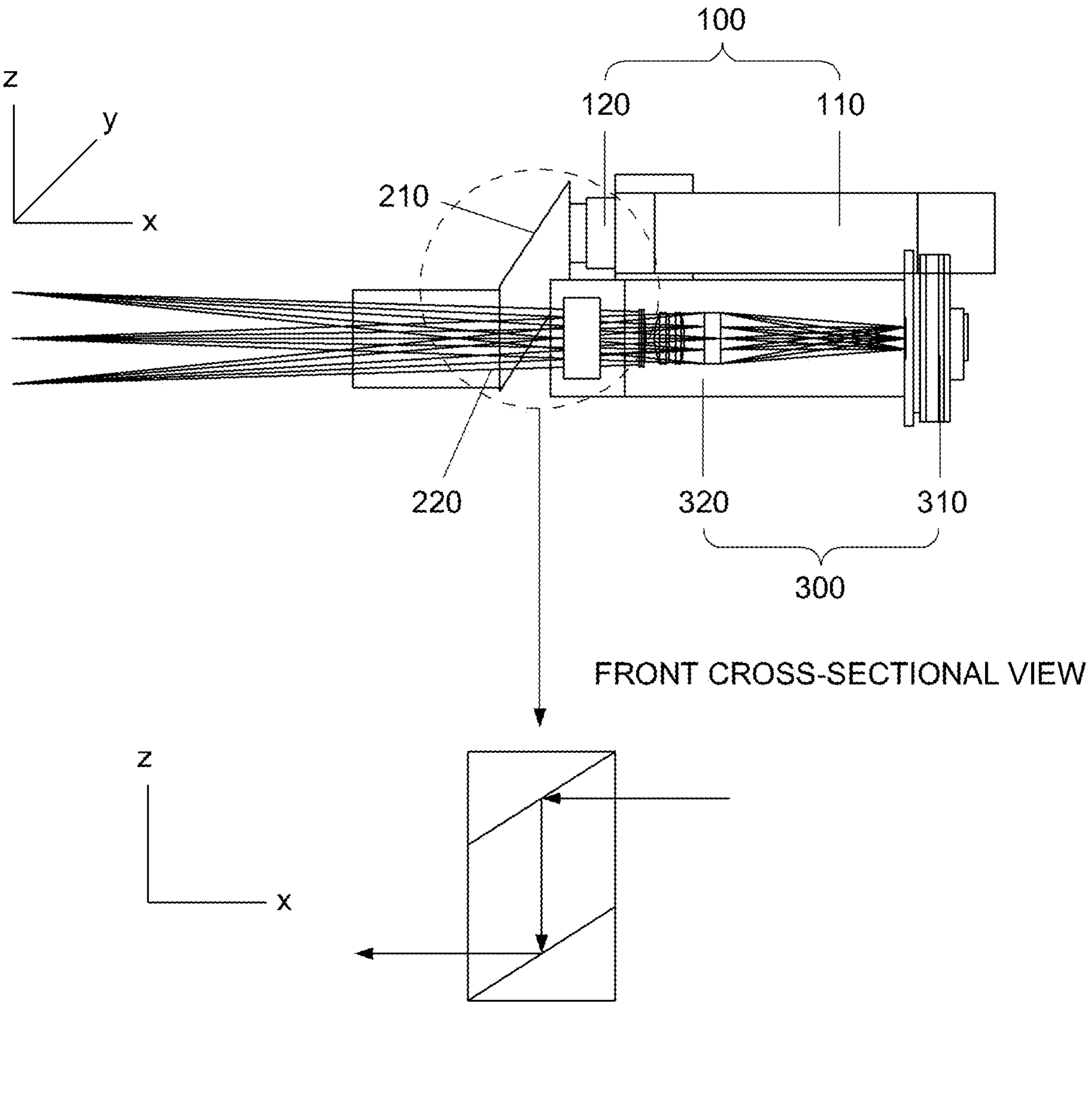
FIG. 4 is a view showing a third reflective mirror and a fourth reflective mirror manufactured and assembled as an integral reflective mirror.

For reference, FIG. 4 is a view showing a third reflective mirror and a fourth reflective mirror manufactured and assembled into an integral reflective mirror. As shown in FIG. 4, the third reflective mirror 210 and the fourth reflective mirror 220 are configured into an integral reflective mirror, thereby being able to improve the assembly efficiency of a scanner.

Meanwhile, the stereo image optical unit 300 includes a first reflective mirror 330, a second reflective mirror 340, a double-sided prism, a first image-forming lens group 320, and one camera sensor 310.

The first reflective mirror 330 and the second reflective mirror 340 are components that reflective light, which travels into them after reflecting from a measurement object in an oral cavity to the double-sided prism positioned on the axis of an image light path. The first reflective mirror 330 and the second reflective mirror 340 should be spaced apart from each other to implement a 3D image. As a preferred example of implementing beams of light traveling inside at different angles, it is useful to implement beams of light such that the beams of light travel inside at symmetric angles having opposite phases $+\alpha$ and $-\alpha$ with respect to an image optical light axis.

The double-sided prism 350 is a component that reflects a first light image and a second light image reflecting from the first reflective mirror 330 and the second reflective mirror 340, respectively, while changing the paths of the light images to an image light path on a first surface 351 of the double-sided prism 350 and a second surface 352 of the double-sided prism 350.

The first light path changer is a component that changes the paths of a first light image and a second light image traveling inside at different angles after reflecting from a measurement object in an oral cavity to an image light path.

As an embodiment of the first light path changer, it may include: a first reflective mirror and a second reflective mirror spaced apart from each other to reflect beams of light traveling inside at different angles after reflecting from a measurement object in an oral cavity to a double-sided prism positioned on an image light path; and a double-sided prism reflecting a first light image and a second light image reflecting from the first reflective mirror and the second reflective mirror, respectively, while changing the paths of the light images to the image light path on a first surface and a second surface.

Figure 5:
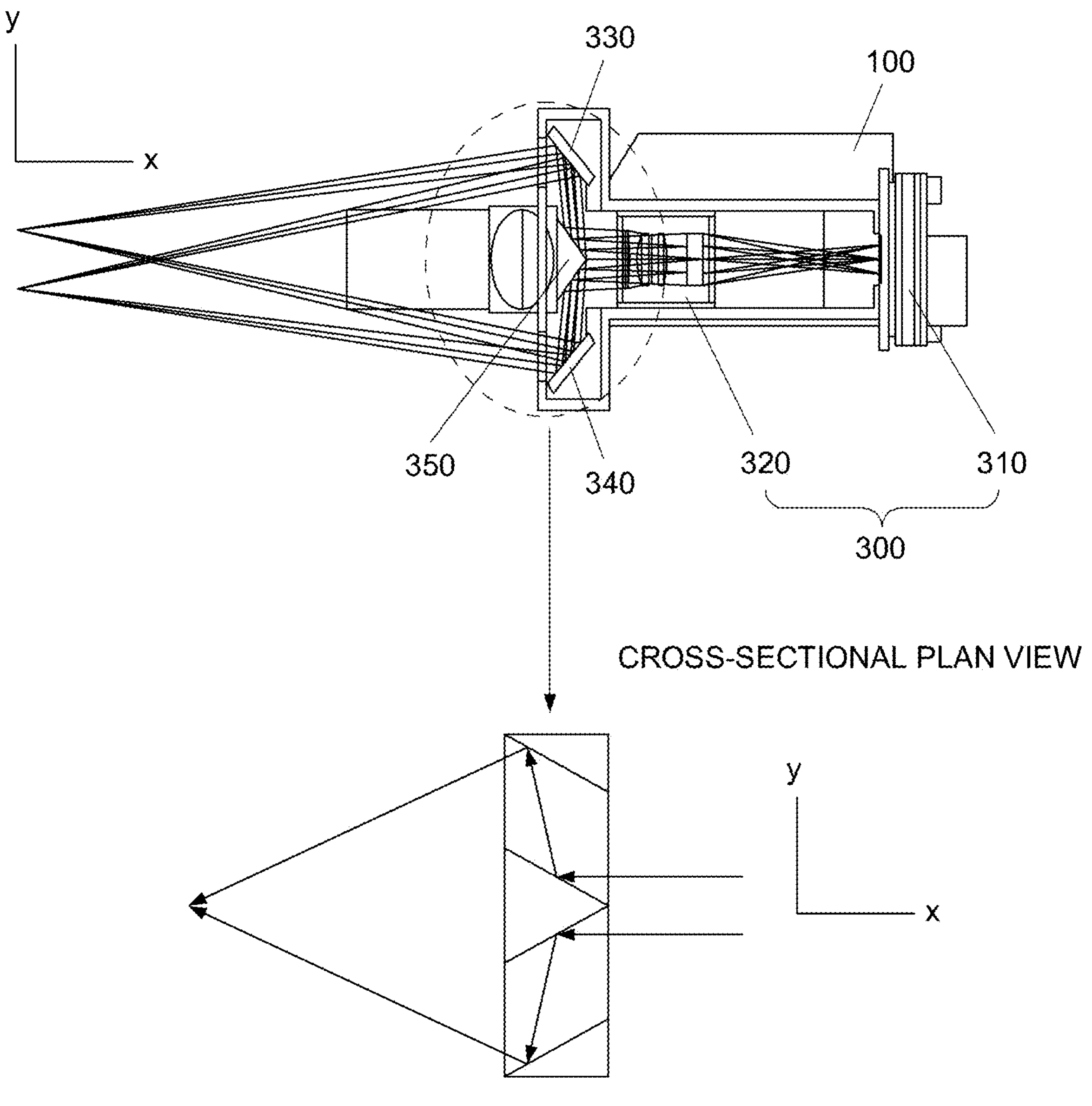
FIG. 5 is a view showing a first reflective mirror, a second reflective mirror, and a double-sided prism integrally manufactured and assembled.

FIG. 5 is a view showing a first reflective mirror, a second reflective mirror, and a double-sided prism integrally manufactured and assembled. As shown in FIG. 5, integrally manufacturing and assembling the first reflective mirror 330, the second reflective mirror 340, and the double-sided prism 350 is a plan for improving the assembly efficiency of an oral scanner.

The camera sensor 310 is a device that obtains an image by taking the first light image and the second light image together which have traveled inside at different angles and of which the paths have been changed on the first surface 351 and the second surface 352 of the double-sided prism 350 described above.

Through this configuration, it is possible to simultaneously obtain two light images, that is, a first light image and a second light image, which have traveled inside at different angles after reflecting from a measurement object in an oral cavity, at one camera sensor 310 through one image-forming lens group 320. At the rear end (not shown) a 3D image is implemented using a structured light pattern using a DMD.

That is, a stereo 3D image is made by one first image-forming lens group 320 and one camera sensor 310, so there is no need for two camera lens groups and two camera sensor like the related art, whereby it is possible to implement a 3D oral scanner in a compact size by reducing the number of parts and using a small space.

Further, there is no need for a board that combines images obtained at a high speed through two different cameras into one synchronized image, so it is possible to improve efficiency such as reducing material costs and shortening the development schedule.

Although the present disclosure was described with reference to limited exemplary embodiments and drawings, the present disclosure is not limited thereto and may be changed and modified in various ways within the spirit of the present disclosure and claims described below by those skilled in the art.

EXPLANATION OF REFERENCE NUMERALS

100 . . . Engine
110 . . . Lighting unit
120 . . . Second image-forming lens group
210 . . . Third reflective mirror
220 . . . Fourth reflective mirror
300 . . . Stereo image optical unit
310 . . . Camera sensor
320 . . . First image-forming lens group
330 . . . First reflective mirror
340 . . . Second reflective mirror
350 . . . Double-sided prism
351 . . . First surface of the double-sided prism
352 . . . Second surface of the double-sided prism

The invention claimed is:

1. A 3D-image oral scanner with a stereo optical system configured using a single camera, the 3D-image oral scanner comprising a stereo image optical unit 3-dimensionally photographing measurement objects in an oral cavity through one camera, wherein the stereo image optical unit includes:

a first light path changer changing paths of a first light image and a second light image traveling inside at different angles after reflecting from a measurement object in an oral cavity to an image light path; and one camera sensor taking the first light image and the second light image together that have traveled inside at different angles and of which the paths have been changed by the first light path changer, wherein the first light path changer includes:

a first reflective mirror and a second reflective mirror spaced apart from each other to reflect beams of light traveling inside at different angles after reflecting from a measurement object in an oral cavity to a double-sided prism positioned on an image light path; and a double-sided prism reflecting a first light image and a second light image reflecting from the first reflective mirror and the second reflective mirror, respectively, while changing paths of the first and second light images to the image light path on a first surface and a second surface thereof, and the one camera sensor takes the first light image and the second light image together which have traveled inside at different angles and of which the paths have been changed on the first surface and the second surface of the double-sided prism.

2. The 3D-image oral scanner of claim 1, wherein the first reflective mirror, the second reflective mirror, and the double-sided prism are integrally manufactured and assembled.

3. The 3D-image oral scanner of claim 1, comprising an engine having a center axis different from the image light path and making and projecting a structured light pattern, wherein the engine includes:

a light unit using a 3-wavelength light source a blue LED; and a second image-forming lens group forming an image using light coming out from the light unit.

4. The 3D-image oral scanner of claim 3, comprising a second light path changer changing a path of light coming out through the second image-forming lens group to a path the same as the image light path.

5. The 3D-image oral scanner of claim 4, wherein the second light path changer includes a third reflective mirror and a fourth reflective mirror.

6. The 3D-image oral scanner of claim 5, wherein the third reflective mirror and the fourth reflective mirror are manufactured and assembly into an integral reflective mirror.

7. The 3D-image oral scanner of claim 1, comprising a first image-forming lens group between the first light path changer and the one camera sensor, and wherein the first light image and the second light image that have traveled inside and of which the paths have been changed by the first light path changer are taken and sent to the one camera sensor through the first image-forming lens group.

* * * * *